US00PP31417P2

(12) United States Plant Patent
Van Dijk

(10) Patent No.: US PP31,417 P2
(45) Date of Patent: Jan. 28, 2020

(54) ***ANTHURIUM* PLANT NAMED 'ANTHEUYK'**

(50) Latin Name: ***Anthurium andraeanum* L.**
Varietal Denomination: ANTHEUYK

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,276

(22) Filed: Oct. 25, 2018

(51) Int. Cl.
*A01H 5/02* (2018.01)
*A01H 6/00* (2018.01)

(52) U.S. Cl.
USPC ..... Plt./367

(58) Field of Classification Search
USPC ..... Plt./365, 367
See application file for complete search history.

(56) References Cited

PUBLICATIONS

UPOV-PLUTO Plant Variety Database, cv name 'ANTHEUYK', 1 page (retrieved from the Internet Jul. 23, 2019).*

EU Community Plant Variety Rights Application No. 2016/2935, Application n°A201603023, filed Nov. 25, 2016, 8 pages.

EU Community Plant Variety Office Official Gazette, Jan. 2017, Feb. 15, 2017, cover page and pp. 30, 50.

EU Community Plant Variety Rights Certificate on the Grant, EU 49817, Jul. 2, 2018, 2 pages.

EU Community Plant Variety Office Official Gazette, May 2018, Oct. 15, 2018, cover page and p. 73.

* cited by examiner

*Primary Examiner* — Susan McCormick Ewoldt

(74) *Attorney, Agent, or Firm* — Jondle & Associates, P.C.

(57) ABSTRACT

A new *Anthurium* plant named 'ANTHEUYK' particularly distinguished by having shiny, weakly blistered, pink, orbicular-cordate and very durable spathes that retain the original color for a very long period of time, dark green and ovate-cordate, durable leaves, pink spadices with orange-yellow tips, early and rich flowering continuously throughout the year, and a plant height of 23.0 cm to 27.0 cm is disclosed.

3 Drawing Sheets

Genus and species: *Anthurium andraeanum* L.
Variety denomination: 'ANTHEUYK'.

BACKGROUND OF THE NEW PLANT

The present invention comprises a new and distinct variety of *Anthurium*, botanically known as *Anthurium andraeanum* L., and hereinafter referred to by the variety name 'ANTHEUYK'. The new *Anthurium* plant is a product of a planned breeding program conducted by the inventor in Bleiswijk, the Netherlands. The objective of this breeding program was to create a new 23.0 cm to 27.0 cm height plant with shiny and weakly blistered, pink, orbicular-cordate and very durable spathes.

The new variety originated from a cross-pollination made in September 2008 in Bleiswijk, The Netherlands. The female parent was a pink *Anthurium* pot plant designated '11376-07' (unpatented), and the male parent was a pink *Anthurium* pot plant designated 'ANTHDATAM' (U.S. Plant Pat. No. 27,699).

A single plant was selected from the progeny of the stated cross in September 2010 and has been asexually reproduced repeatedly by tissue culture in Bleiswijk, The Netherlands, over a 6-year period. The present invention has been found to retain its distinctive characteristics through successive asexual propagations.

Plant Breeder's Rights for this variety have been applied for in the European Union on Nov. 25, 2016. 'ANTHEUYK' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny and weakly blistered, pink, orbicular-cordate spathes;
2) Pink spadices with orange-yellow tips; and
3) Green, ovate-cordate leaves.

DESCRIPTION OF THE PHOTOGRAPHS

This new *Anthurium* plant is illustrated by the accompanying photographs which show the overall plant habit including blooms, bud and foliage of the plant; the colors shown are as true as can be reasonably obtained by conventional photographic procedures. The photographs are of a 28-week old plant grown in a greenhouse in Bleiswijk, The Netherlands, in September 2018. Colors in the photographs may differ from the color values cited in the detailed botanical description, which accurately describe the actual colors of the new variety.

DESCRIPTION OF THE NEW VARIETY

Figure 1:
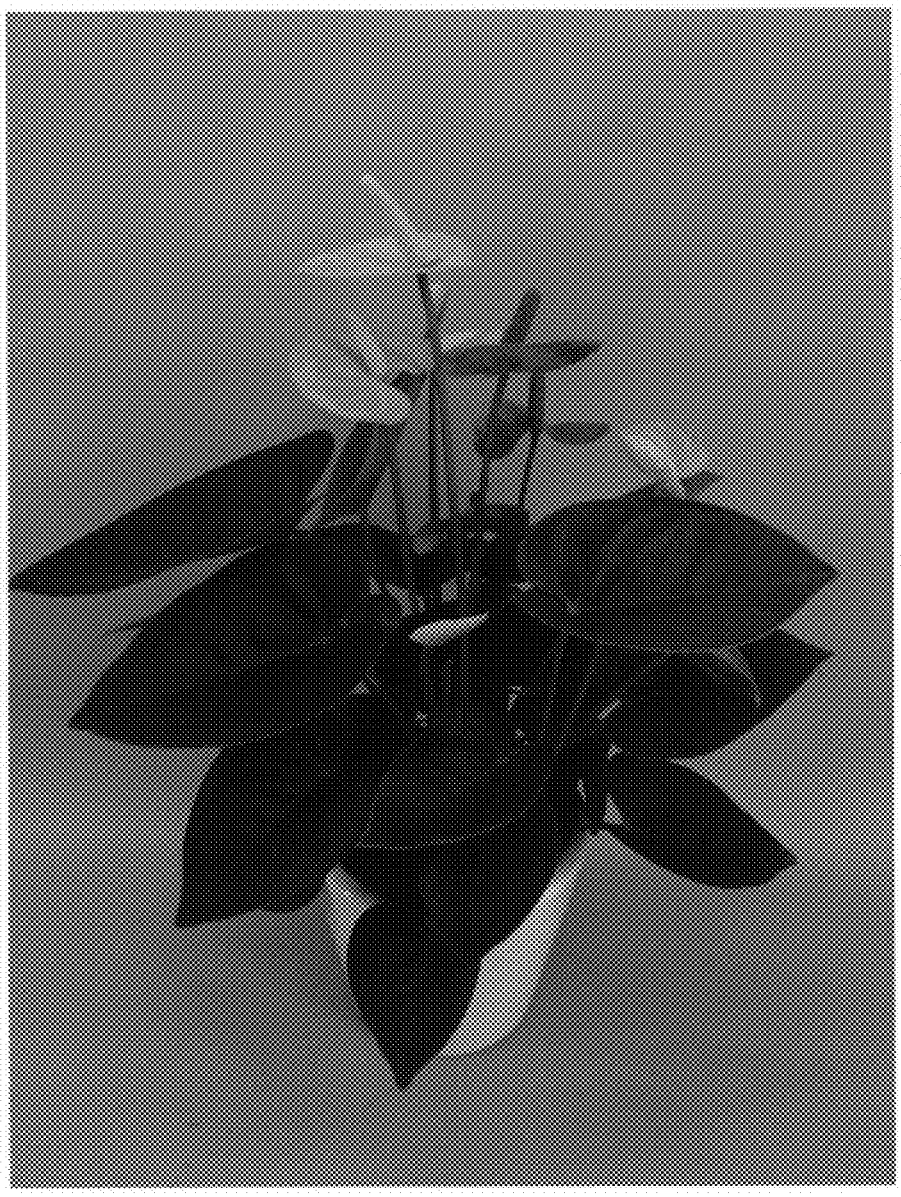
FIG. 1 shows the overall plant habit, including blooms, bud and foliage.
Figure 2:
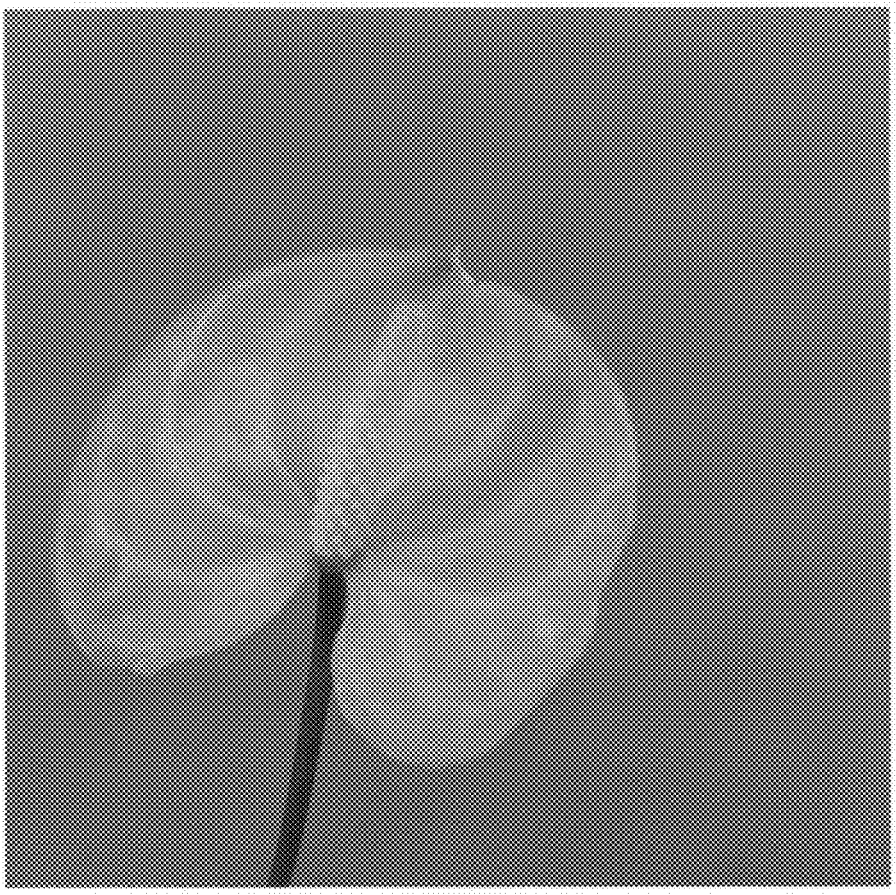
FIG. 2 shows a close-up of the mature spathe.
Figure 3:
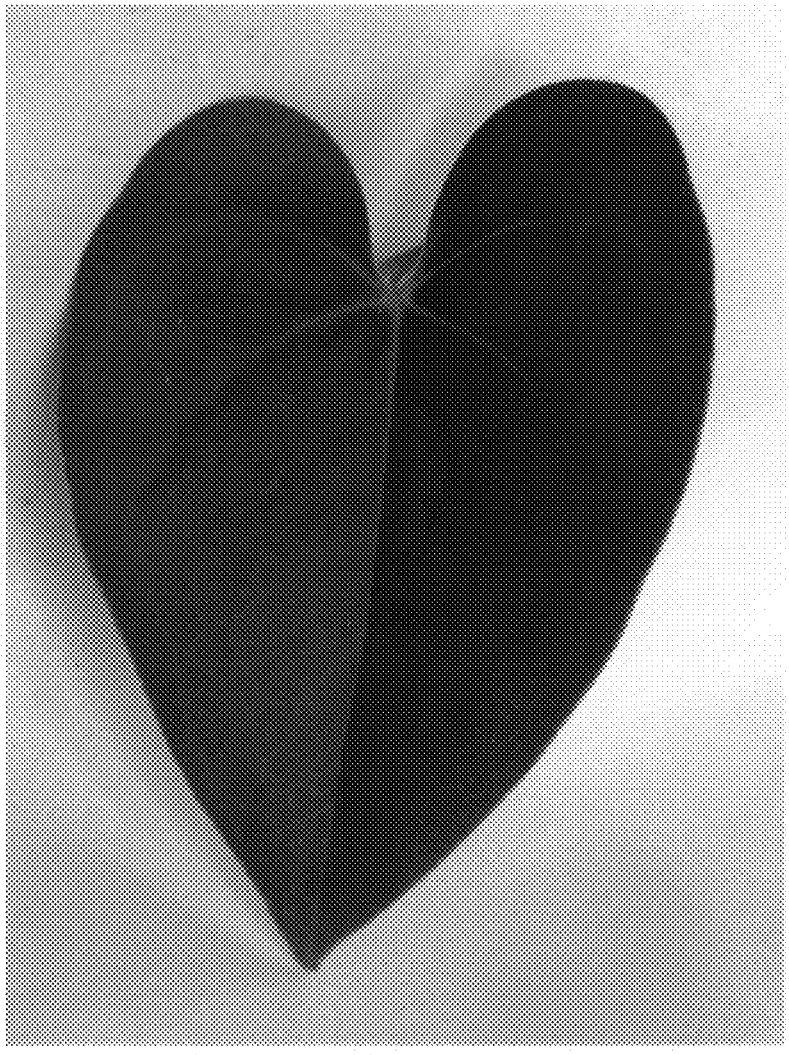
FIG. 3 shows a close-up of the upper leaf blade surface.

The following detailed description sets forth the distinctive characteristics of 'ANTHEUYK'. The data which define these characteristics were collected from asexual reproductions carried out in Bleiswijk, The Netherlands. The plant history was taken on 28-week old plants which were planted from tissue culture in 9 centimeter (diameter) pots and grown in a glass greenhouse between 19° C. and 24° C. Observations were made in September 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHEUYK'.

Parentage:

*Female parent*.—*Anthurium* plant '11376-07' (unpatented).

*Male parent*.—*Anthurium* plant 'ANTHDATAM' (U.S. Plant Pat. No. 27,699).

Plant:

*Propagation*.—Tissue culture.

*Root description*.—Fleshy, greyed-yellow colored roots with small hairy lateral roots having yellow colored root tips.

*Time to produce a finished flowering plant*.—27 to 29 weeks after planting in a 9 cm (diameter) pot.

*Growth habit*.—Upright.

*Height* (*measured from soil, including inflorescence*) .—23.0 cm to 27.0 cm.

*Width* (*measured from leaf tips*).—25.0 cm to 28.0 cm.

Leaves:

*Immature leaves*.—Length: 7.0 cm to 8.0 cm. Width: 4.5 cm to 5.5 cm. Color: Upper surface: RHS 146A. Lower surface: RHS 146B. Texture (both upper and lower surfaces): Shiny and soft.

*Mature leaves*.—Length (fully expanded): 11.0 cm to 13.0 cm. Width: 7.5 cm to 8.5 cm. Shape: Ovate-cordate. Apex: Acute. Base: Cordate. Leaf blade angle with the petiole: Between 100 degrees and 120 degrees. Leaf margin: Entire. Color: Upper surface: RHS 147A. Lower surface: RHS 146A. Texture (both upper and lower surfaces): Leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 2.0 cm to 3.0 cm. Width of lobes of mature leaf blades: 3.0 cm to 4.0 cm. Distance from petiole/leaf junction to highest point on lobes of mature leaf: 1.5 cm to 2.5 cm.

*Petiole*.—Cross-section: Round. Diameter: 0.3 cm to 0.4 cm. Length: 11.0 cm to 14.0 cm for a mature leaf size. Color: Mature leaf: RHS 144A. Immature leaf: RHS 144B. Cataphyll color surrounding the petiole: Outside: RHS 145A. Inside: RHS 145B.

*Geniculum*.—Length: 1.5 cm to 2.0 cm. Width: 0.2 cm to 0.3 cm. Color: RHS 144A.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters (3.0 cm to 4.0 cm).

*Arrangement*.—Spathe angle with the peduncle is between 95 degrees and 115 degrees; the spathe stands on a wiry peduncle about 3.0 cm to 8.0 cm above the foliage.

*Shape*.—Orbicular-cordate.

*Apex*.—Mucronate.

*Base*.—Cordate.

*Texture*.—Shiny and weakly blistered.

*Margin*.—Undulated.

*Size*.—Length: 4.5 cm to 5.5 cm. Width: 6.0 cm to 6.5 cm.

*Lobes*.—Present.

*Arrangement*.—The spathe has two lobes extending past the peduncle. The lobes are non-touching. Length: 1.0 cm to 2.0 cm. Width: 2.0 cm to 3.0 cm.

*Color*.—Just fully open: Upper surface: RHS 38A. Lower surface: RHS 38C. This pink color remains for a very long period, at least more than 30 weeks after opening Peduncle:

*Shape*.—Erect.

*Cross-section*.—Round.

*Length*.—19.0 cm to 24.0 cm.

*Diameter*.—0.3 cm to 0.4 cm.

*Color*.—RHS 144A.

Flowering time:

*General*.—One small, rooted, untreated tissue culture plant of 8.0 cm tall will flower, depending on the season, after 27 to 29 weeks and 5 to 6 blossoms appear. More blossoms appear after some additional weeks so that a full flowering and commercial plant will have 6 to 7 pink spathes. Smaller blossoms may occur on immature plants.

Spadix:

*Size*.—Length: 2.5 cm to 3.5 cm (depending on flower size). Width (at apex): 0.4 cm to 0.5 cm. Width (at base): 0.5 cm to 0.6 cm.

*Shape*.—Columnar.

*Angle from spadix tip to peduncle*.—150 degrees to 160 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 17B. Mature: RHS 38B. Ages to: RHS 146B.

Flowers:

*Quantity per spadix*.—100 to 150.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: 100 to 150. Length: Less than 0.01 cm. Color: RHS 158C.

*Style*.—Not observed to date.

*Stigma*.—Shape: Ovoid. Diameter: Less than 0.01 cm. Color: RHS 158C.

*Ovary*.—Rarely visible.

*Ovary color*.—Not measured.

Fruit and seed set: None observed to date.

COMPARISON WITH PARENTAL AND COMMERCIAL VARIETIES

The female parent plant of 'ANTHEUYK', cultivar '11376-07', is no longer in existence, so a meaningful comparison cannot be made.

'ANTHEUYK' differs from the male parent plant 'ANTHDATAM' (U.S. Plant Pat. No. 27,699) in that 'ANTHEUYK' has acute leaf apexes and spathes with an upper surface color of RHS 38A, whereas 'ANTHDATAM' has acuminate leaf apexes and spathes with an upper surface color of RHS 52A.

'ANTHEUYK' differs from similar commercial variety 'ANTHDINWAQ' (U.S. Plant Pat. No. 26,048) in that 'ANTHEUYK' has acute leaf apexes and spathes with an upper surface color of RHS 38A, whereas 'ANTHDINWAQ' has acuminate leaf apexes and spathes with an upper surface color of RHS 51A. Additionally, 'ANTHEUYK' has a longer plant height than 'ANTHDINWAQ'.

'ANTHEUYK' differs from similar commercial variety 'ANTHEOCMA' (unpatented) in that 'ANTHEUYK' has ovate-cordate leaves and orbicular-cordate spathes with an upper surface color of RHS 38A, whereas 'ANTHEOCMA' has elliptical-cordate leaves and ovate spathes with an upper surface color of RHS 38D.

I claim:

1. A new and distinct variety of *Anthurium* plant named 'ANTHEUYK', substantially as illustrated and described herein.

* * * * *